(12) United States Patent
Geiger et al.

(10) Patent No.: US 8,036,436 B2
(45) Date of Patent: Oct. 11, 2011

(54) SYSTEM AND METHOD FOR SEGMENTING A REGION IN A MEDICAL IMAGE

(75) Inventors: Paul Geiger, Toronto (CA); Vittorio Accomazzi, Toronto (CA)

(73) Assignee: Cedara Software Corp., Mississauga, Ontario (CA)

( * ) Notice: Subject to any disclaimer, the term of this patent is extended or adjusted under 35 U.S.C. 154(b) by 1022 days.

(21) Appl. No.: 11/870,193

(22) Filed: Oct. 10, 2007

(65) Prior Publication Data

US 2008/0267468 A1     Oct. 30, 2008

Related U.S. Application Data

(60) Provisional application No. 60/828,894, filed on Oct. 10, 2006.

(51) Int. Cl.
    G06K 9/00 (2006.01)
    G06K 9/34 (2006.01)
(52) U.S. Cl. ......... 382/128; 382/173; 382/131; 382/132
(58) Field of Classification Search .................. None
    See application file for complete search history.

(56) References Cited

U.S. PATENT DOCUMENTS

| | | | |
|---|---|---|---|
| 5,602,979 A * | 2/1997 | Loop | 345/423 |
| 5,871,019 A | 2/1999 | Belohlavek | |
| 6,251,072 B1 | 6/2001 | Ladak et al. | |
| 6,272,233 B1 | 8/2001 | Takeo | |
| 6,373,491 B1 * | 4/2002 | Sasaki | 345/443 |
| 6,404,936 B1 * | 6/2002 | Katayama et al. | 382/283 |
| 6,561,980 B1 | 5/2003 | Gheng et al. | |
| 6,778,690 B1 | 8/2004 | Ladak et al. | |
| 6,792,071 B2 * | 9/2004 | Dewaele | 378/62 |
| 7,162,065 B2 | 1/2007 | Ladak et al. | |
| 7,397,935 B2 * | 7/2008 | Kimmel et al. | 382/128 |
| 7,468,075 B2 * | 12/2008 | Lang et al. | 623/16.11 |
| 7,618,451 B2 * | 11/2009 | Berez et al. | 623/14.12 |
| 2004/0218797 A1 | 11/2004 | Ladak et al. | |
| 2008/0260230 A1 * | 10/2008 | Gotardo et al. | 382/131 |

OTHER PUBLICATIONS

Mingyue Ding; Congjin Chen; Yunqiu Wang; Igor Gyacskov; Aaron Fenster, "Prostate segmentation in 3D US images using the cardinal-spline-based discrete dynamic contour", Medical Imaging: Visualization, Image-Guided Procedures, and Display. Feb. 2003, pp. 69-76.*

(Continued)

*Primary Examiner* — Samir Ahmed
*Assistant Examiner* — Li Liu
(74) *Attorney, Agent, or Firm* — Michael Best & Friedrich LLP (57) ABSTRACT

A method and computer program are provided for segmenting a prostate from a medical image such as an ultrasound image. Each slice in a study is analysed and uses a manual initialization to obtain an initial contour, in which a user selects initial points that are automatically rendered on the image. An automatic refinement stage then snaps the contour to the prostate boundary in the image based on a pre-stored anatomical atlas and edge information obtained from the image. A manual adjustment stage may then be performed and if selected, the contour is automatically propagated to the next image slice to avoid the manual initialization. An auxiliary image slice may be referred to, which indicates how the prostate shape changes from slice to slice, e.g. by providing a perpendicular profile.

25 Claims, 7 Drawing Sheets

OTHER PUBLICATIONS

Latulipe et al. "symSpline: Symmetric Two-Handed Spline Manipulation", CHI 2006, p. 349-358.*

Cootes, T.F.; Taylor, C.J.; "Statistical Models of Appearance for Computer Vision"; Imaging Science and Biomedical Engineering; Mar. 8, 2004; pp. 13 to 28; Chapter 4; University of Manchester.

Ladak, Hanif M. et al.; "Prostate Segmentation from 2D Ultrasound Images"; Proceedings of the $22^{nd}$ Annual EMBS International Conference; Jul. 23-28, 2000; Chicago, IL.

International Search Report from PCT/CA2007/001772 dated Nov. 26, 2007, received by the applicant on Jan. 25, 2008.

* cited by examiner

SYSTEM AND METHOD FOR SEGMENTING A REGION IN A MEDICAL IMAGE

This application claims priority from U.S. Application No. 60/828,894 flied on Oct. 10, 2006, the contents of which are incorporated herein by reference.

FIELD OF THE INVENTION

The present invention relates to image segmentation and has particular utility in segmenting a region in a medical image.

DESCRIPTION OF THE PRIOR ART

As the frequency of prostate cancer diagnoses in men increases, so to does the need for early detection. Symptoms due to carcinoma of the prostate are generally absent until extensive growth occurs and once the tumour extends beyond the prostate the risk of further complications increases. However, when diagnosed at an early stage, prostate cancer is curable and even at later stages, treatment can be effective. Treatment options can vary depending on the extent of the cancer and the prognosis generally worsens when the diagnosis is at an advanced stage.

The challenges that face physicians for handling prostate cancer diagnoses include being able to diagnose patients at an early and thus curable stage, accurately evaluate the stages and grades of the disease, apply the correct therapy, and monitor a patient's progress during therapy. Imaging technologies such as ultrasound have been paramount in enabling a physician to overcome such challenges.

An important aspect in the use of medical images for diagnosing prostate cancer (and other diseases) is the accurate segmentation of the region of interest in the image (e.g. the prostate) to identify the boundaries of the region and other anatomical structures. Assignment of the appropriate therapy or dose to the prostate typically requires that the prostate volume be accurately measured. Accurate segmentation of a region of interest is also important in other types of imaging and image analysis.

For some anatomical structures where the image contrast is great, such as fluid filled regions, the segmentation of that structure can be relatively simple and thus numerous segmentation approaches can be used. However, an ultrasound image of structures having low contrast such as the prostate can be difficult to segment. Typical local image processing techniques such as edge detectors have been found to be inadequate in and of themselves for finding the boundary, due to speckle, shadowing and other image artefacts.

It is therefore an object of the following to obviate or mitigate the above-mentioned disadvantages.

SUMMARY OF THE INVENTION

In one aspect, there is provided a method for segmenting a region in an image comprising generating an initial contour from a plurality of initial points by interpolating a contour segment between each pair of neighbouring ones of the plurality of initial points using one or more control points placed relative to the each pair; and adjusting the positions of the control points to modify each the contour segment to refine the initial contour according to information regarding an expected shape for the region.

In another aspect, there is provided a computer readable medium comprising computer executable instructions for causing an image processing device to segment a region in an image by generating an initial contour from a plurality of initial points by interpolating a contour segment between each pair of neighbouring ones of the plurality of initial points using one or more control points placed relative to the each pair; and adjusting the positions of the control points to modify each the contour segment to refine the initial contour according to known information regarding an expected shape for the region.

In yet another aspect, there is provided a method for generating a initial contour for segmenting a region in an image comprising enabling the selection of a first point at a first extent of the region; enabling the selection of a second point at a second extent of the region being opposite the first point to define a line of symmetry; generating a provisional contour passing through the first and second points; providing a third point on the provisional contour on one side of the line of symmetry; enabling movement of the third point towards a third extent of the region; during movement of the third point, automatically moving a fourth point on the provisional contour on the other side of the line of symmetry in a direction opposite that of the third point towards a fourth extent of the region; and interpolating between the points according to information indicative of an expected shape for the region to generate the initial contour.

In yet another aspect, there is provided a method for refining a segmentation contour generated on an image for a region in the image comprising comparing the contour to boundary information in the image to generate a first score; comparing the contour to information indicative of an expected shape for the region to generate a second score; combining the first and second scores to obtain a combined score; reshaping the contour a plurality of times to obtain a plurality of adjusted contours; generating the combined score for each the plurality of adjusted contours; and generating a refined contour according to the highest of the combined scores.

In yet another aspect, there is provided a method for segmenting a three dimensional region from a stack of image slices of the region comprising obtaining an auxiliary image slice of the region at a different angle than the stack to provide a profile of the region in another dimension; and referencing the profile to approximate a next segmentation contour for a next one of the image slices while propagating through the stack of image slices.

BRIEF DESCRIPTION OF THE DRAWINGS

An embodiment of the invention will now be described by way of example only with reference to the appended drawings wherein.

DETAILED DESCRIPTION OF THE INVENTION

Figure 1:
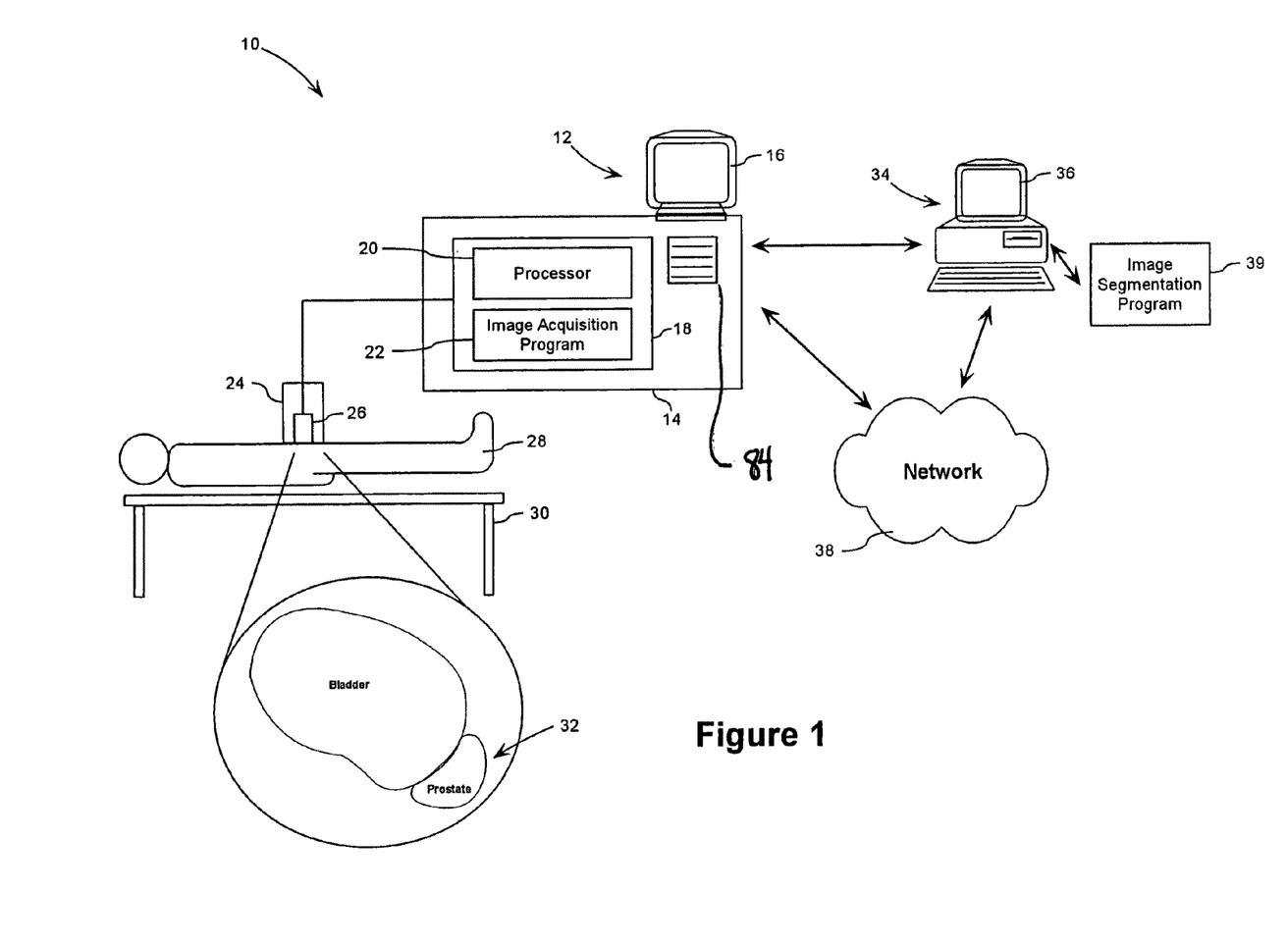
FIG. 1 is a schematic view of an ultrasound imaging environment.

Referring therefore to FIG. 1, an imaging environment, in this example an ultrasound imaging environment is generally denoted by numeral 10. The environment 10 comprises an ultrasound imaging apparatus 12, an examination table 30 and a patient 28 positioned on the table 30. The apparatus 12 comprises an ultrasound machine 14, a display and control interface 16, and an ultrasound probe 24. The probe 24 includes one or more transducers 26 that emit sound waves and receive echoes of such sound waves as is well known in medical imaging.

The machine 14 comprises an imaging module 18 for controlling the probe 24. The imaging module 18 comprises a processor 20 and a computer implemented image acquisition program 22 for obtaining one or more images of a region of interest in the patient 28. Preferably, the ultrasound apparatus 12 is capable of obtaining 3-D ultrasound images wherein an array of transducers 26 or a moveable transducer 26 is used in order to obtain an array or stack of 2-D image slices 84 (see also FIG. 10) that represent the 3-D ultrasound image of the region of interest. In FIG. 1, the region of interest includes the prostate 32.

The 2-D image slices 84 are typically stored electronically in the machine 14 and/or remotely in an image archiving system (not shown) accessible over a network 38. In the following examples, the image slices 84 are accessible to a viewing station 34 with a display 36 that also has access to an image segmentation program 39 for segmenting, analyzing, diagnosing, treating etc., the region of interest as seen in the image slices 84. It will be appreciated that, as shown in FIG. 1, the computer station 34 may be directly linked to the imaging apparatus 12, e.g. in an examination room, or indirectly linked, via the network 38, to the data obtained by the apparatus 12, e.g. at a remote office or clinic.

Figure 2:
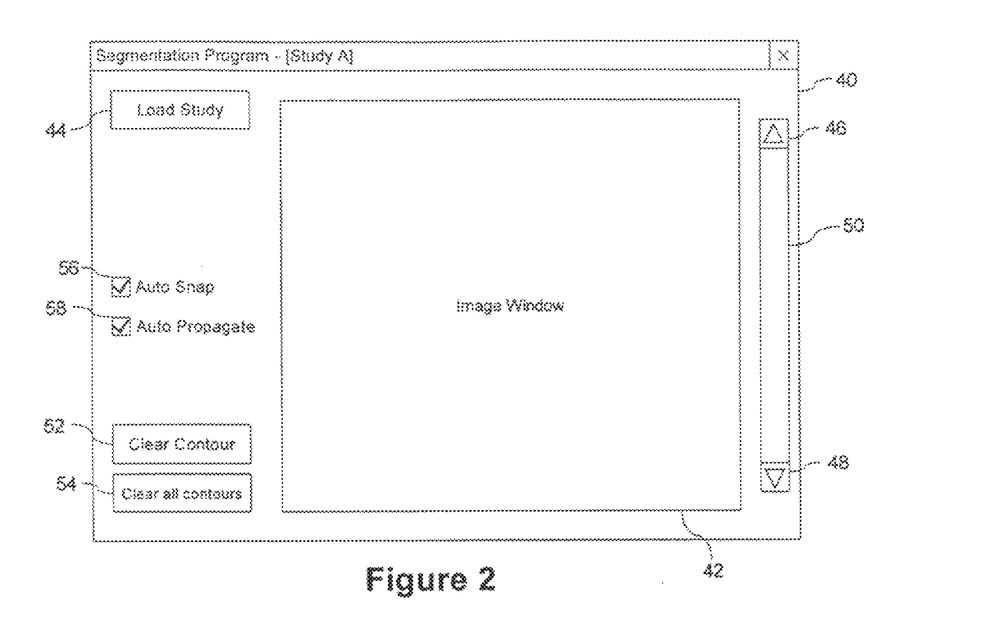
FIG. 2 is a schematic view of a graphical user interface for the image segmentation program of FIG. 1.

The display 36 preferably provides a graphical user interface (GUI) 40 for enabling a user to load and analyze the image slices 84. A set, array or stack of image slices 84 may also be referred to as a study. The GUI 40 comprises an image window 42 for displaying a medical image 60, e.g. that shown in FIG. 3. In this exemplary interface, successive images in a study are viewed by selecting a back arrow 46, a forward arrow 48 and/or a scroll bar 50. A "load study" button 44 enables a user to load a new study, which imports a series of image slices 84 for a particular patient 28. A "clear contour" button 52 enables a user to remove a contour that has been placed in the image window 42 and a "clear all contours" button 54 enables the user to remove all contours on all image slices 84 in the study. Such contours are explained in greater detail below. In this example, an "auto snap" checkbox 56 is provided to enable the user to snap selection points to an edge in the image and an "auto propagate" checkbox 58 enables the user to select or deselect the propagation of a contour to the next image slice 84. These features are explained in greater detail below.

Figure 3:
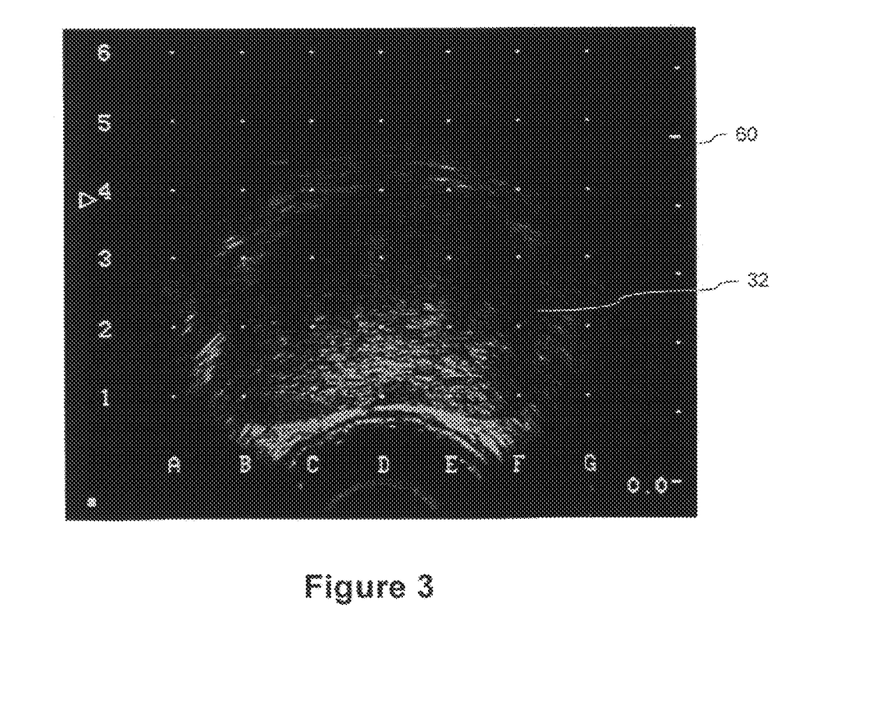
FIG. 3 is an ultrasound image of a prostate.

As noted above, FIG. 3 provides an exemplary ultrasound image 60. As can be seen in FIG. 3, the prostate 32 can be visually segmented, however, due to the low contrast with its surroundings, it may be difficult to segment from the image using conventional techniques.

Figure 4:
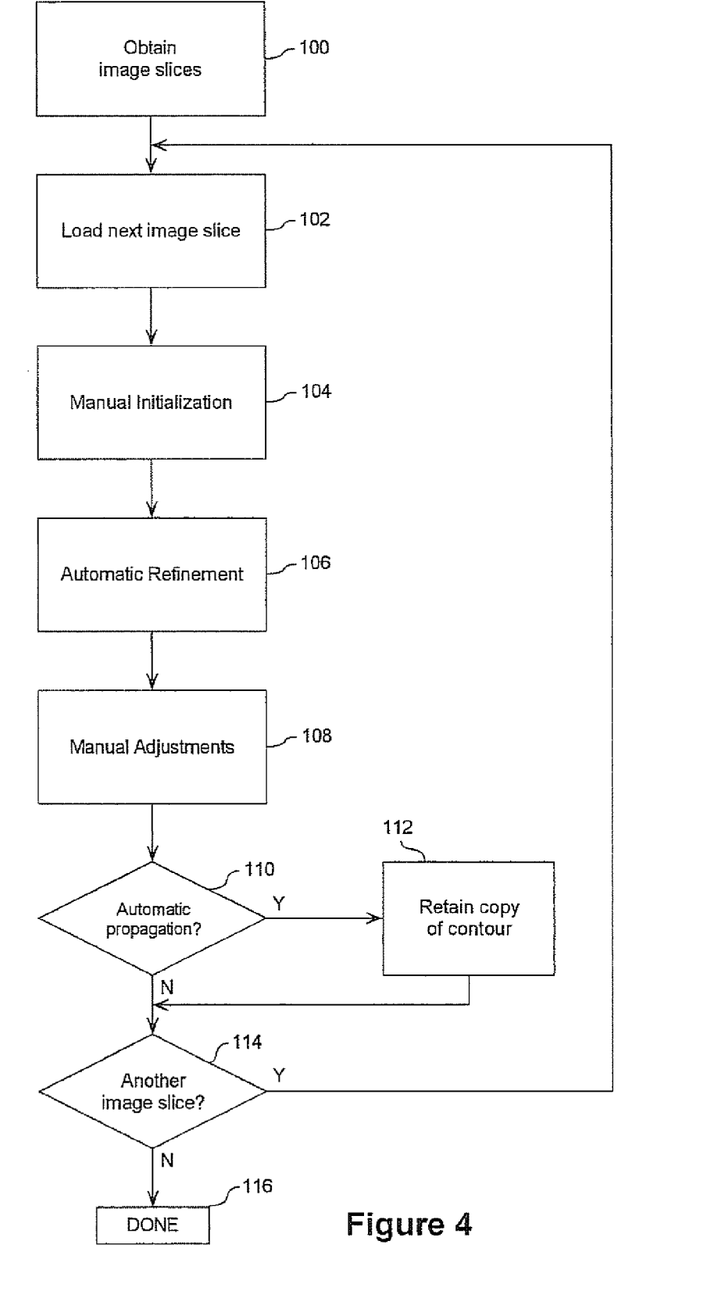
FIG. 4 is a flowchart illustrating steps in a prostate segmentation procedure.

An image segmentation procedure, having particular utility in segmenting the prostate 32 from an ultrasound image 60, is shown in FIGS. 4 through 9. Referring first to FIG. 4, a set of image slices 84 or study is obtained at step 100. The image slices 84 are generated using the apparatus 12 and stored as a study. In the following example, the study is accessed by a user at the viewing station 34. Once the image slices 84 are obtained at step 100, the next slice (beginning with an initial slice, e.g. from the middle of the stack) is loaded into the image window 42 at step 102. It will be appreciated that the segmentation procedure can also be used during real-time image acquisition and need not operate only with pre-acquired/pre-stored images.

Figure 5:
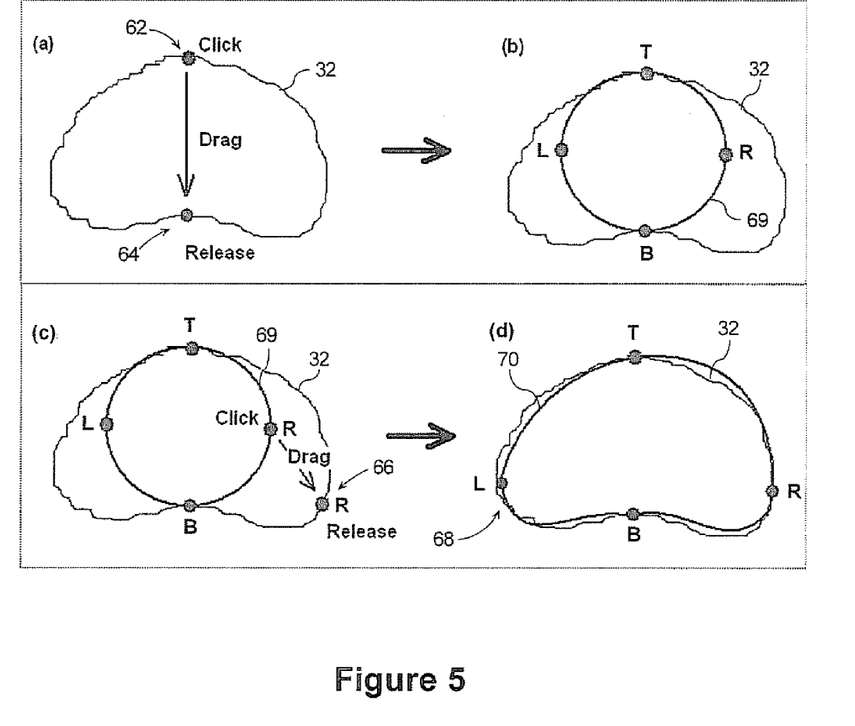
FIG. 5 pictorially illustrates the manual initialization procedure of FIG. 4.
Figure 6:
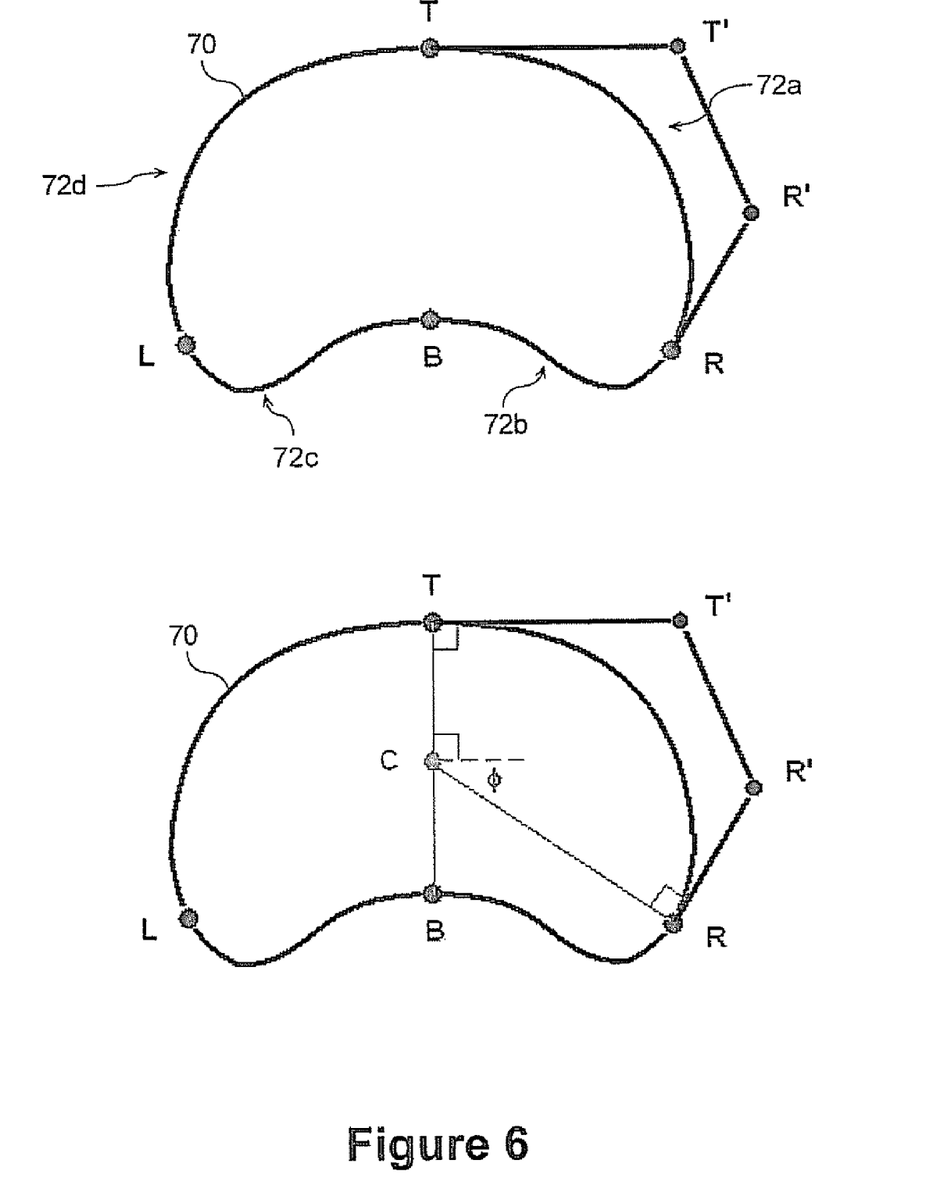
FIG. 6 pictorially illustrates a curve fitting procedure.

Using the GUI 40, the user can then begin the segmentation procedure by first performing a manual initialization at step 104. The manual initialization step 104 is shown in FIGS. 5 and 6. The manual initialization step 104 maximizes user interactions to create an improved workflow, in particular by reducing the number of user interactions using known information. In this way, the user's knowledge can be harnessed and taken advantage of to improve the segmentation while providing a convenient workflow.

At step (a) the user first selects a point in a first uppermost extent 62 of the region in the image (e.g. prostate in this example) that is as near as possible to the boundary and close to the line of symmetry in the structure 32 as shown schematically in FIG. 5. Preferably, a "drag and release" action is used to select a second point in a second lower extent 64 that is at the other end of the line of symmetry. During the drag and release, a provisional contour 69 is generated over the image 60 as shown in step (b) of FIG. 5, preferably in real time to help guide the user in selecting the second point. The provisional contour 69 in this embodiment is circular in shape with a diameter defined by the placement of top point T and bottom point B, which also define a line of symmetry and pass through the first and second points selected by the user. The provisional contour 69 also identifies a third, right point R and a fourth, left point L, which are reflections of each other through the line of symmetry defined by line TB.

As seen in step (c) of FIG. 5, the user is then able to select the third or right point R and perform another drag and release action towards a third rightmost extent 66. When the user completes the drag and release, as shown in step (d), an initial contour 70 is generated, which is a re-shape or refinement of the provisional contour 69, which provides a first approximation of the region, e.g. prostate 32.

Referring now to FIG. 6, the re-shaping or refilling of the contour is performed on four contour segments 72a-d, which are delineated by the three user selected points T, B, R and the automatically placed point R. Each of the segments 72a-d is generated by interpolating between each pair of neighbouring ones of the initial points. It has been found that a spline-based interpolation is preferable, in particular one that obtains a cubic Bezier curve, which defines itself using four points, often referred to as control points. In FIG. 6, the generation of segment 72a is shown. The Bezier curve for segment 72a includes points T and R and outside control points T' and R'. The curve starts at T and arrives at R coming from the direction of R'. In general, the segment 72a will not pass through either T' or R' but these outside control points are present to provide directional information.

It has been found that the arrangement shown in the lower diagram of FIG. 6 produces good prostate shapes. To calculate T' and R', the following procedure can be used:

1) The line TT' is perpendicular to the line TB;
2) The line RR' is perpendicular to the line CR, where C is the midpoint of the line TB;
3) the length of RR' is computed as $0.28*|T-B|$; and
4) the length of TT' is computed as $$0.28*|R-L|*\left(\frac{90}{90-|\phi|}\right),$$

where ϕ is the angle shown in FIG. 6, measured in degrees. The remaining Bezier curves defining segments 72b-d are constructed similarly.

The formulae used above were chosen empirically based on a comparison of the resulting contour 70 in relation to expected, actual boundary shapes for the region being segmented, the prostate in this example. It will be appreciated that when adapted to different applications or for segmenting other structures, the formulae may require modifications to suit the particular shape. The flexibility of the Bezier curve enables the program 39 to change the shape of the contour 70 by moving the control points T' and R', in order to find the best match. It will be appreciated that any interpolation that can be adjusted or controlled using such control points or similar features can be adapted to provided similar flexibility.

Turning back to FIG. 4, when the manual initialization step 104 has been completed by the user, and if the auto snap checkbox 56 is selected, an automatic refinement step 106 may then be performed by the segmentation program 39 to provide a better fit for the contour 70 with respect to the actual boundary by "snapping" the contour 70 to a boundary detected in the image 60. In step 106, the program 39 searches for shapes that are close to the manual contour, and which maximize a certain score function. The score is used to determine a better fit for the contour 70 to the prostate 32, and the better fit is then rendered on the image 60.

In the following example, the score is based on two criteria: a) a measurement of how well the boundary of the shape coincides with the boundaries in the image (the boundaries in the image are estimated using the gradient strength and gradient direction from the edge boundary 82); and b) the plausibility of the shape as determined from information indicative of the expected shape for the region, e.g. prostate, and a numerical rating for each potential shape. As will be described below, in one embodiment, the information is obtained from the contents of an atlas.

It will be appreciated that the information can be provided by any one or more of the following; functional knowledge derived from medical images, known or detected geometry of the region, known or detected symmetry of the region, real-time information acquired during imaging, the empirically derived atlas of expected shapes, and localization information. This information can be pre-stored or automatically detected or obtained in real-time depending on the application.

Figure 9:
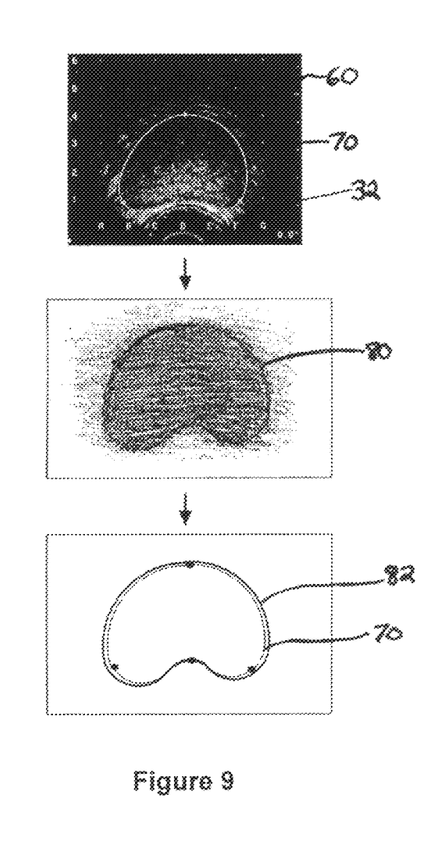
FIG. 9 illustrates pre-processing performed during the automatic refinement procedure of FIG. 4.

In this example, the score element a) is computed by obtaining edge information as shown in FIG. 9 and comparing the contour 70 to that edge boundary. As seen in FIG. 9, the program 39 first processes the image 60 to obtain anatomical edge information. Preferably, a median filter is first applied to suppress weak and irrelevant edges to obtain an intermediate boundary 80 from the raw image data. A gradient-magnitude filter may then be applied to obtain an edge image 82 that can be used to calculate the score element a).

The score element a) can be calculated as follows: for each pixel in the gradient-magnitude image that is touched by the contour 70, the score is incremented by the value of that pixel. As such, the score element a) is large if the contour is close to edges in the image 60.

Since there may be more than one boundary detected by the program 39, and to avoid snapping to an incorrect boundary, preferably, one or more atlases of prostate shapes is used to compute score element b).

The atlases are used to capture plausible shapes of the prostate to avoid the automatic refinement step 106 from being "distracted" by boundaries which are not related to the prostate. Such irrelevant boundaries can be caused, e.g., by seeds implanted in the prostate or calcification.

The atlases are preferably pre-stored in memory and can generally be updated and improved as more empirical data becomes available. It has been found that the atlas can be generated using the methodology for Statistical Shape Models described in Chapter 4 of the paper: COOTES et al., "Statistical Models of Appearance for Computer Vision", Imaging Science and Biomedical Engineering, University of Manchester, Mar. 8, 2004, pages 13-28.

In general, the model is created by drawing a set of shapes, aligning the shapes, and generalizing the shape using a Principle Component Analysis (PCA): x=x̄+Φb (1), where x̄ is the average shape and Φ is the matrix whose columns are the eigenvectors associated with the largest eigenvalues. The number of eigenvectors to retain is determined by requiring that approximately 80% or approximately 90% of the observed shape variations are retained, so that the high frequency shapes are automatically eliminated. In general, Φ is a rectangular matrix having more rows than columns.

Assuming a Gaussian distribution of shapes used to Generate the atlas, it can be shown that for a given shape generated by equation (1), the probability of such a shape being part of the atlas can be determined by:

$$\log(p(b)) = c * \sum \frac{b_i^2}{\lambda_i} + const; \qquad (2)$$

where $b_i$ are the components of the b vector and $\lambda_i$ the eigenvalues associated with the eigenvectors of Φ (see section 4.6 of the Cootes et al. paper). Equation (2) can be used to evaluate the plausibility of a given shape. For example, the following algorithm can be used:

1) Invert matrix Φ using singular value decomposition (SVD), where the SVD decomposition inhibits numerical instability and deals with non square matrices;
2) Given a shape x, calculate: b=Φ$^{-1}$(x̄−x); and
3) Evaluate the plausibility of shape x as $$Pl = \sum \frac{b_i^2}{\lambda_i}. \qquad (3)$$

Figure 8:
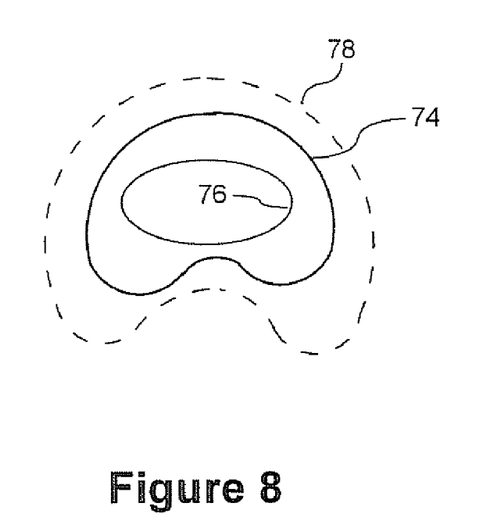
FIG. 8 illustrates an average prostate shape and inner and outer ranges therefor.

In general, as shown in FIG. 8, the average prostate shape 74 is determined and the contour 70 is evaluated against a range of shapes from an inner limit 76 to an outer limit 78.

Figure 7:
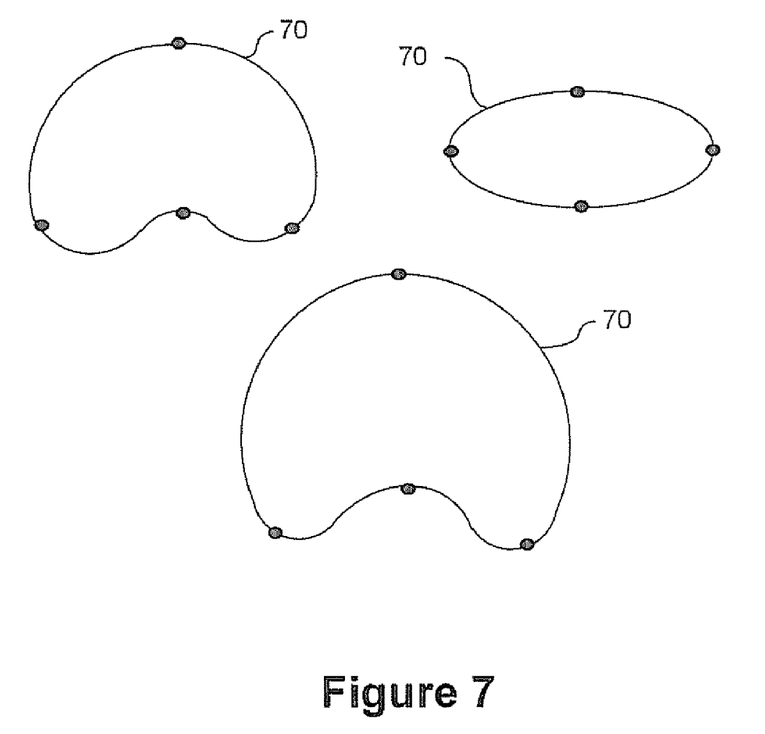
FIG. 7 illustrates exemplary prostate shapes in a shape atlas.

In the present example, the prostate can assume different shapes, and all of them are equally plausible. The shape depends on the acquisition, image modality and also pathology. For example, the shapes shown in FIG. 7 are valid prostate shapes.

Since equation (3) effectively evaluates the distance of a given shape from the average shape, it is generally not preferred to insert into a single atlas, shapes that are quite different. Instead, it is preferable to create multiple atlases which each include similar shapes, e.g. "round" prostate shapes. The score element b) may then be chosen as the best score obtained across all atlases.

The total score is a weighted combination of score elements a) and b). The weights reflect the importance of each element and may vary based on the application. It has been found that trial and error provides a suitable way to determine an appropriate weighting scheme.

The locations for control points T' and R' are adjusted and a score for each adjusted contour is computed. Preferably, the control points T' and R' are moved within a certain window such as approximately +/−10% of the prostate diameter (found to provide an adequate compromise between accuracy and speed) and the contour 70 regenerated until the score is maximized. For example, T' and R' are stepped through a discrete set of values whose range is the above-mentioned +/−10% of the prostate diameter, and whose step size is about 1% of the prostate diameter. Thus, the contour is regenerated a number of times, e.g., 20×20=400 times. It should be noted that the contour 70 is preferably not redrawn each time it is regenerated but rather the score of, e.g. approximately 400 candidates is instead evaluated and the one with the best score redrawn. The contour 70 then "snaps" to the approximate prostate boundary to complete step 106.

Turning back to FIG. 4, the program 39 preferably enables the user to perform manual adjustments to the contour 70 in step 108 after the automatic refinement is rendered on the image 60. The user can manually adjust the contour 70 by dragging any of the points T, B, L and R, or points along the contour 70 towards the visually identified boundary. Preferably, when the user selected points T, B, L and R are dragged, the two adjacent segments (e.g. T and 72a and 72d) are reshaped whilst the other two segments remain fixed. This occurs due to the fact that the user selected point is a control point iii both Bezier curves. Also, when a point along the contour 70 between one of the user selected points is dragged (i.e. along a segment), only that segment is automatically reshaped and the remaining three segments remain fixed. The reshaping is controlled by the program 39, which manipulates the control points for the Bezier curves to enforce the smoothness of the segment(s). For example, the Bezier-curve equation can be solved to find the points T' and R' which cause the curve to pass through the point that is being dragged.

At step 110, the program 39 determines if the user has selected the auto propagation checkbox 58. If the box 58 has been selected then the program 39 retains the final contour 70 rendered on the image and propagates that contour 70 to the next image slice. This avoids the manual initialization step 104. The auto propagation feature is most useful where the study does not have a large slice gap. Where the study has a large slice gap, the auto propagation feature may be undesirable, and at step 114 if another slice is to be segmented, the process repeats, including the manual initialization step 104. Wen all slices have been segmented, the segmentation procedure is completed at step 116. The segmented image slices 84 may then be used for later analysis, e.g. for computing an estimate of the prostate volume. The prostate volume measured at different times can indicate the progression and/or response to treatment.

Figure 10:
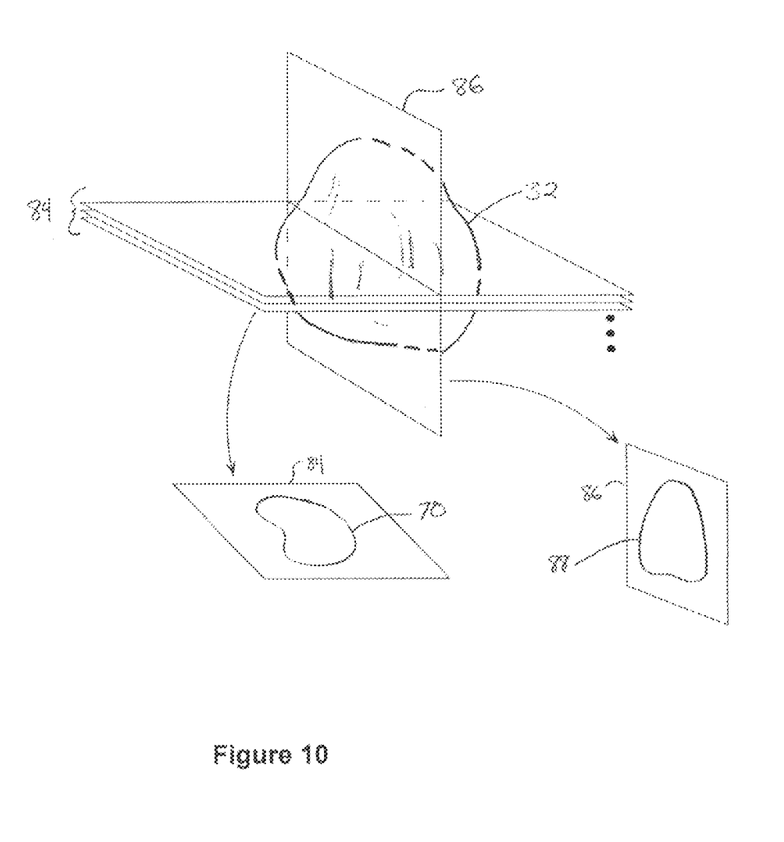
FIG. 10 illustrates an auxiliary image slice for profiling a prostate in an additional dimension.

To accommodate for varying slice gaps, at least one auxiliary slice 86 may be obtained as shown in FIG. 10. The study that includes a series of image slices 84 provides a 2-D image of the prostate 32 at various elevations. Since the shape of the prostate 32 is likely not uniform, the size of the prostate 32 in the image 60 for a slice 84 in the middle region may be much larger than the prostate 32 as seen in a slice 84 closer to the top. The auxiliary slice 86 is taken at one or more different angles than the stack or array of slices 84, preferably perpendicular to the other image slices 84, and provides an additional profile(s) 88 of the prostate 32 in another dimension. The additional profile(s) 88 allows the program 39 to determine when the top (or bottom) of the prostate has been found.

Subsequent slices 84 would then be irrelevant and the program 39 can automatically determine when the study is complete.

Similarly, the additional profile 88 enables the program 39 to automatically control the auto propagation feature 58 and is capable of adjusting the previous contour by re-sizing by a certain factor to accommodate a large variance in prostate size between successive image slices 84. The additional profile 88 also enables the contour to be re-shaped if necessary as indicated by the change in the profile 88 as the program propagates through the slices 84. As such, a better approximation can be propagated to the next image slice 84 which in turn enables a more accurate automatic refinement to occur. It will be appreciated that the profile 88 may not necessarily be perpendicular but may be at another angle to the slices 84 as dictated by the auxiliary slice 86.

It is therefore seen that a semi-automatic segmentation procedure can provide accurate segmentation using information indicative of expected shapes along with manual selections by the user. The user's knowledge and input from the minimal interactions can be harnessed to provide a better approximation and thus better segmentation. The minimal user interactions also improves workflow and makes the process more convenient for the user. Preferably, spline-based interpolation such as that using a Bezier curve is used to approximate the shape and renders the contour 70 in real time as the user selects the initial points and the program 39 automatically refines the contour 70. As another preference, an auxiliary slice 86 can be used to predict the variance in structure size from slice to slice providing a better "starting point" for the next segmentation iteration.

It will be appreciated that the above principles can be used to segment any region of interest in many types of images and the foregoing examples are given as illustrative examples only. For example, the above procedure may be used for segmenting a similarly shaped structure from other medical images such as MRI, CT, X-ray etc. As such, the information, e.g. from an anatomical atlas, can be used to provide predictive information based on the shape that is of interest. The atlas would thus be populated based on empirically derived "common" shapes, similar to those described above for the prostate. Real-time information may also be used rather than pre-stored information depending on the application of the segmentation procedure and the anatomy being imaged.

Although the invention has been described with reference to certain specific embodiments, various modifications thereof will be apparent to those skilled in the art without departing from the spirit and scope of the invention as outlined in the claims appended hereto.

The invention claimed is:

1. A computer-implemented method for segmenting a region in an image comprising:
   defining a plurality of initial points on the image;
   defining, with a processor, one or more control points placed relative to each pair of neighbouring ones of said plurality of initial points;
   generating, with the processor, an initial contour from the plurality of initial points by interpolating a Bezier curve between each pair of neighbouring ones of said plurality of initial points using the one or more control points placed relative to said each pair, wherein said interpolating comprises using a spline-based interpolation between said each pair wherein said control points are located outside of said initial contour; and
   adjusting, with the processor, the positions of said control points to modify each said Bezier curve to refine said initial contour according to information regarding an expected shape for said region.

2. The method according to claim 1 wherein defining a plurality of initial points includes
enabling the selection of a first point at a first extent of said region;
enabling the selection of a second point at a second extent of said region being opposite said first point to define a line of symmetry;
enabling the selection of a third point at a third extent of said region on one side of said line of symmetry; and
providing a fourth point at a fourth extent of said region across said line of symmetry from said third point.

3. The method according to claim 2 comprising
examining boundary information in said image to generate a score,
refining said initial contour a plurality of times to produce a plurality of scores and generating a refined contour according to the highest of said scores.

4. The method according to claim 3 wherein said examining boundary information comprises
comparing said initial contour to boundary information in said image to generate a first score;
comparing said initial contour to said information to generate a second score, said information being indicative of an expected shape for said region;
combining said first and second scores to obtain a combined score;
reshaping said initial contour a plurality of times to obtain a plurality of adjusted contours;
generating said combined score for each said plurality of adjusted contours; and
generating said refined contour according to the highest of said combined scores.

5. The method according to claim 4 wherein said first score is calculated by incrementing by the value of each pixel in a gradient-magnitude image such that said first score is high when said contour is close to edges in said image.

6. The method according to claim 4 wherein said second score is calculated according to how close said contour is from an average shape, said average shape being determined from a plurality of shapes in an empirically derived atlas of expected shapes.

7. The method according to claim 4 wherein said combined score is computed as a weighted combination of said first and second scores.

8. The method according to claim 2 wherein said information is provided by one or more of the following: functional knowledge derived from medical images, geometry of said region, symmetry of said region, real-time information acquired during imaging, an empirically derived atlas of expected shapes, and localization information.

9. The method according to claim 2 wherein said control points are modified a plurality of times and at each modification, a plausibility of the shape of said region is determined from an atlas of empirically derived expected shapes for said region, said plausibility being used to choose a refined contour.

10. The method according to claim 2 wherein providing said fourth point comprises enabling selection of said fourth point at said fourth extent of said region across said line of symmetry from said third point.

11. The method according to claim 2 wherein enabling the selection of said third point and providing said fourth point comprise
generating a provisional contour passing through said first and second points;
providing said third point on said provisional contour on said one side of said line of symmetry;
enabling movement of said third point towards said third extent of said region; and
during movement of said third point, automatically moving said fourth point on said provisional contour on an other side of said line of symmetry in a direction opposite that of said third point towards said fourth extent of said region.

12. The method according to claim 1 comprising
obtaining at least one auxiliary image slice of said region at a different angle than a stack of image slices containing said region to provide a profile of said region in another dimension;
repeating said method for each said image slices and referencing said profile to approximate a next segmentation contour for a next one of said image slices while propagating through said stack of image slices.

13. A non-transitory computer readable medium comprising computer executable instructions for causing an image processing device to segment a region in an image by
defining a plurality of initial points on the image;
defining one or more control points placed relative to each pair of neighboring ones of said plurality of initial points;
generating an initial contour from the plurality of initial points by interpolating a Bezier curve between each pair of neighbouring ones of said plurality of initial points using the one or more control points placed relative to said each pair, wherein said interpolating comprises using a spline-based interpolation between said each pair wherein said control points are located outside of said initial contour; and
adjusting the positions of said control points to modify each said Bezier curve to refine said initial contour according to known information regarding an expected shape for said region.

14. The computer readable medium according to claim 13 wherein the instructions for defining a plurality of initial points on the image include instructions for
enabling the selection of a first point at a first extent of said region; enabling the selection of a second point at a second extent of said region being opposite said first point to define a line of symmetry;
enabling the selection of a third point at a third extent of said region on one side of said line of symmetry; and
providing a fourth point at a fourth extent of said region across said line of symmetry from said third point.

15. The computer readable medium according to claim 14 comprising instructions for
examining boundary information in said image to generate a score,
refining said initial contour a plurality of times to produce a plurality of scores and generating a refined contour according to the highest of said scores.

16. The computer readable medium according to claim 15 wherein said examining boundary information comprises
comparing said initial contour to boundary information in said image to generate a first score;
comparing said initial contour to said information to generate a second score, said information being indicative of an expected shape for said region;
combining said first and second scores to obtain a combined score;
reshaping said initial contour a plurality of times to obtain a plurality of adjusted contours;

generating said combined score for each said plurality of adjusted contours; and generating said refined contour according to the highest of said combined scores.

17. The computer readable medium according to claim 16 wherein said first score is calculated by incrementing by the value of each pixel in a gradient-magnitude image such that said first score is high when said contour is close to edges in said image.

18. The computer readable medium according to claim 16 wherein said second score is calculated according to how close said contour is from an average shape, said average shape being determined from a plurality of shapes in an empirically derived atlas of expected shapes.

19. The computer readable medium according to claim 16 wherein said combined score is computed as a weighted combination of said first and second scores.

20. The computer readable medium according to claim 14 wherein said information is provided one or more of the following: functional knowledge derived from medical images, geometry of said region, symmetry of said region, real-time information acquired during imaging, an empirically derived atlas of expected shapes, and localization information.

21. The computer readable medium according to claim 14 wherein said control points are modified a plurality of times and at each modification, a plausibility of the shape of said region is determined from an atlas of empirically derived expected shapes for said region, said plausibility being used to choose a refined contour.

22. The computer readable medium according to claim 14 wherein providing said fourth point comprises enabling selection of said fourth point at said fourth extent of said region across said line of symmetry from said third point.

23. The computer readable medium according to claim 14 wherein the instructions enabling selection of said third point and providing said fourth point comprise generating a provisional contour passing through said first and second points;

providing said third point on said provisional contour on said one side of said line of symmetry;

enabling movement of said third point towards said third extent of said region; and during movement of said third point, automatically moving said fourth point on said provisional contour on an other side of said line of symmetry in a direction opposite that of said third point towards said fourth extent of said region.

24. The computer readable medium according to claim 13 comprising instructions for obtaining at least one auxiliary image slice of said region at a different angle than a stack of image slices containing said region to provide a profile of said region in another dimension;

repeating said method for each said image slices and referencing said profile to approximate a next segmentation contour for a next one of said image slices while propagating through said stack of image slices.

25. A computer-implemented method for generating a initial contour for segmenting a region in an image comprising:

enabling, with a processor, the selection of a first point at a first extent of said region;

enabling, with the processor, the selection of a second point at a second extent of said region being opposite said first point to define a line of symmetry;

generating, with the processor, a provisional contour passing through said first and second points;

providing, with the processor, a third point on said provisional contour on one side of said line of symmetry;

enabling, with the processor, movement of said third point towards a third extent of said region;

during movement of said third point, automatically moving, with the processor, a fourth point on said provisional contour on the other side of said line of symmetry in a direction opposite that of said third point towards a fourth extent of said region; and interpolating, with the processor, between said points according to information indicative of an expected shape for said region to generate said initial contour, wherein the processor generates said initial contour by interpolating a Bezier curve between pairs of said points.

* * * * *